(12) United States Patent
Touma

(10) Patent No.: US 9,322,758 B2
(45) Date of Patent: Apr. 26, 2016

(54) METHOD AND APPARATUS FOR FULL SCALE DYNAMIC FOOTING LOAD TEST

(71) Applicant: John Fahd Fadlo Touma, Riyadh (SA)

(72) Inventor: John Fahd Fadlo Touma, Riyadh (SA)

( * ) Notice: Subject to any disclaimer, the term of this patent is extended or adjusted under 35 U.S.C. 154(b) by 413 days.

(21) Appl. No.: 13/862,386

(22) Filed: Apr. 13, 2013

(65) Prior Publication Data

US 2014/0305186 A1 Oct. 16, 2014

(51) Int. Cl.
*G01N 3/303* (2006.01)
*E02D 1/00* (2006.01)

(52) U.S. Cl.
CPC . *G01N 3/303* (2013.01); *E02D 1/00* (2013.01)

(58) Field of Classification Search
USPC .......................................... 73/12.06
See application file for complete search history.

(56) References Cited

U.S. PATENT DOCUMENTS

| | | | |
|---|---|---|---|
| 4,116,041 A | 9/1978 | Tholen | |
| 4,359,890 A | 11/1982 | Coelus | |
| 6,286,613 B1 * | 9/2001 | Tsai et al. | 175/20 |
| 2004/0099063 A1 * | 5/2004 | Frederick | 73/818 |
| 2006/0096394 A1 * | 5/2006 | Nelson, Jr. | G01N 1/2252 73/864.34 |
| 2006/0191316 A1 * | 8/2006 | Miyasaka et al. | 73/11.03 |
| 2011/0194902 A1 * | 8/2011 | Mitri | 405/259.5 |
| 2013/0086974 A1 * | 4/2013 | Rausche | 73/12.01 |

OTHER PUBLICATIONS

Crovetti, et al., Comparison of Two Falling Weight Deflectometer Devices, Dyantest 8000 and KUAB 2M-FWD, Nov. 1989, American Society for Testing and Materials, pp. 59-69.*
George, Falling Weight Deflectometer for Estimating Subgrade Resilient Moduli, Oct. 2003, University of Mississippi.*
Long-Term Pavement Performance Program Manual for Falling Weight Deflectometer Measurements, Dec. 2006, U.S. Department of Transportation, Version 4.1.*
Inventor Statement Regarding Prior Art, included in Information Disclosure Statement filed herewith.
Inventor Catalog of Systems to Test Pile Foundations accompanying above-listed Inventor Statement Regarding Prior Art.

* cited by examiner

*Primary Examiner* — Hezron E Williams
*Assistant Examiner* — David Z Huang
(74) *Attorney, Agent, or Firm* — Lewis, Reese & Nesmith, PLLC

(57) ABSTRACT

A method for determining allowable bearing pressures of a steel footing on variable subsurface materials whether native soils, rock, or manmade construction material is disclosed. The method continuously measures vertical displacement by an optical technique of a dismantable steel footing under the impact of a free falling steel drop weight. The load pulse of the drop weight is measured by means of a load cell.

16 Claims, 3 Drawing Sheets

METHOD AND APPARATUS FOR FULL SCALE DYNAMIC FOOTING LOAD TEST

BACKGROUND

Advances in site investigation techniques have afforded engineers tools to assess the suitability of shallow foundations designs with regards to the reliability under design load cases and economic considerations. Full scale, static load tests have been performed as part of research studies, but do not enjoy widespread use as acceptance criteria for constructed foundations in the profession. The operational expenses are one factor that accounts for the reluctance of engineering professionals to rely on footing load tests. Dynamic load tests provide benefits similar to a full scale load test. A dynamic test method is described using a specially designed apparatus. The apparatus described consists of an easily dismantable steel footing 100 with associated accessories for safely delivering a dynamic load and measurement of the load and footing response. All of the system components in the apparatus are capable of being reused multiple times at different locations and project sites. The associated electronic instrumentation allows direct measurement of the vertical displacement 99 and load pulse at the precision and accuracy required by the engineering profession.

SUMMARY OF THE INVENTION

The test method consists of the assembly of a steel footing 100, anvil 200, and safety frame 300 at the test location. Electronic instrumentation is fastened at designated points on the footing 100 and within the anvil 200. A steel drop weight 400 is assembled by addition of steel plates 480 to a drop weight frame 430, which frame 430 is secured together using bolts 486 welded onto a lower plate 485 of the frame. Assembly of all steps is performed by hand unaided by any special lifting equipment. The assembled drop weight frame 430 is lifted above the steel footing 100, within the confines of the safety frame 300, and dropped onto the anvil 200 at a height of up to 1.5 m. The load pulse generated by the free falling drop weight 400 striking the anvil 200 is measured by a load cell 220 embedded within the anvil 200, and a vertical displacement 99 of the steel footing 100 is measured by a position sensitive detector 140. The acquired signals from the load cell 220 and position sensitive detector 140 are used to generate a plot of load and vertical displacement 99 with time. A qualified geotechnical engineer inspects the plot. In light of other data, such as engineering properties of the subsurface material, the geotechnical engineer will determine allowable performance criteria to assess if the vertical displacement 99 is satisfactory under the imposed load.

DETAILED DESCRIPTION OF THE INVENTION

Figure 1:
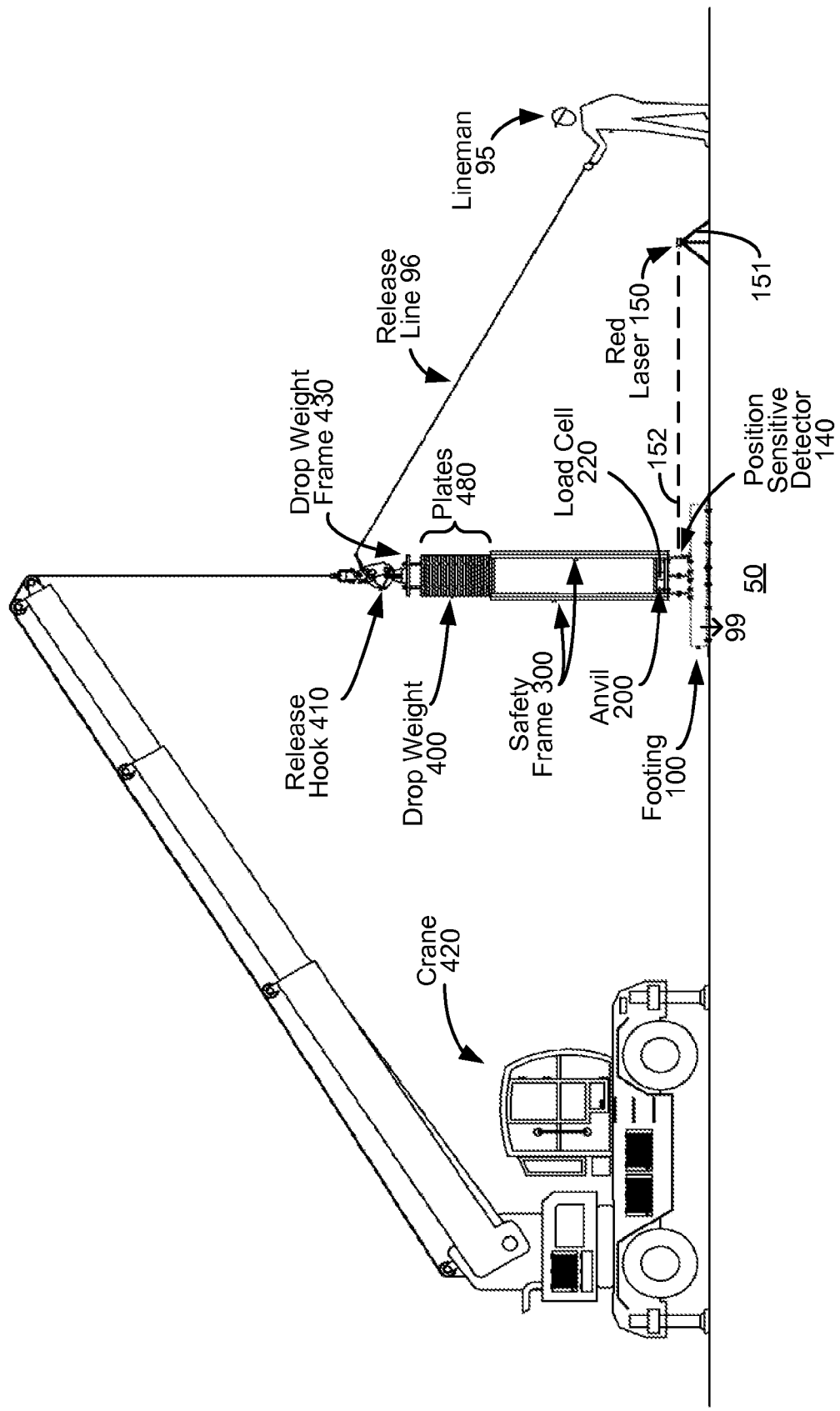
FIG. 1 illustrates the setup of the primary components including the steel footing 100, the anvil 200, the safety frame 300, and the drop weight 400. The primary components consist entirely of steel sections including plate, angle, and channel sections as well as associated nuts and bolts. The secondary components consist of electronic instrumentation and acquisition devices (the position sensitive detector 140, laser 150, and load cell 220), as well as the quick release hook 410.
Figure 2:
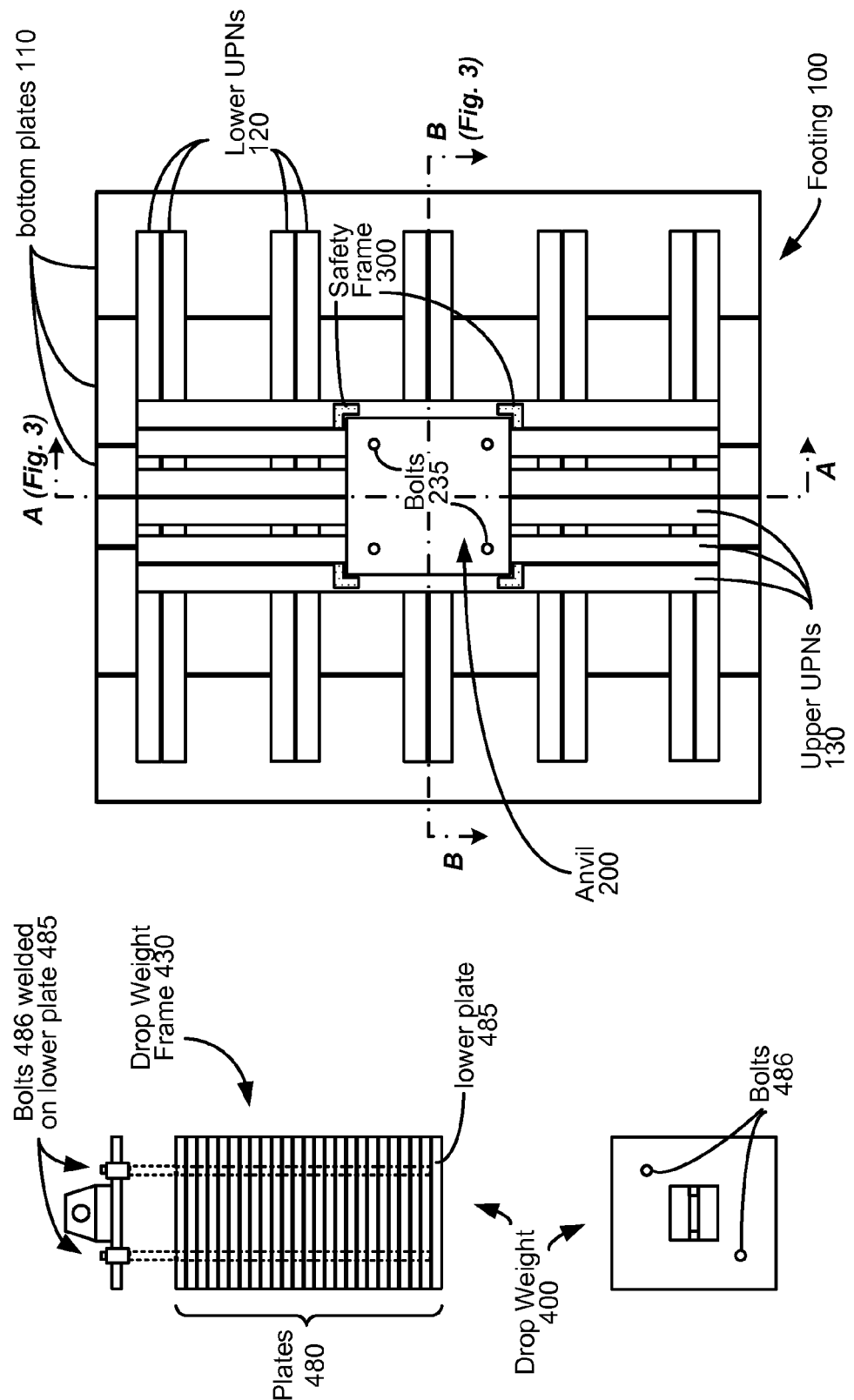
FIG. 2 presents a plan view of the footing 100 as well as plan and section views of the steel drop weight 400.
Figure 3:
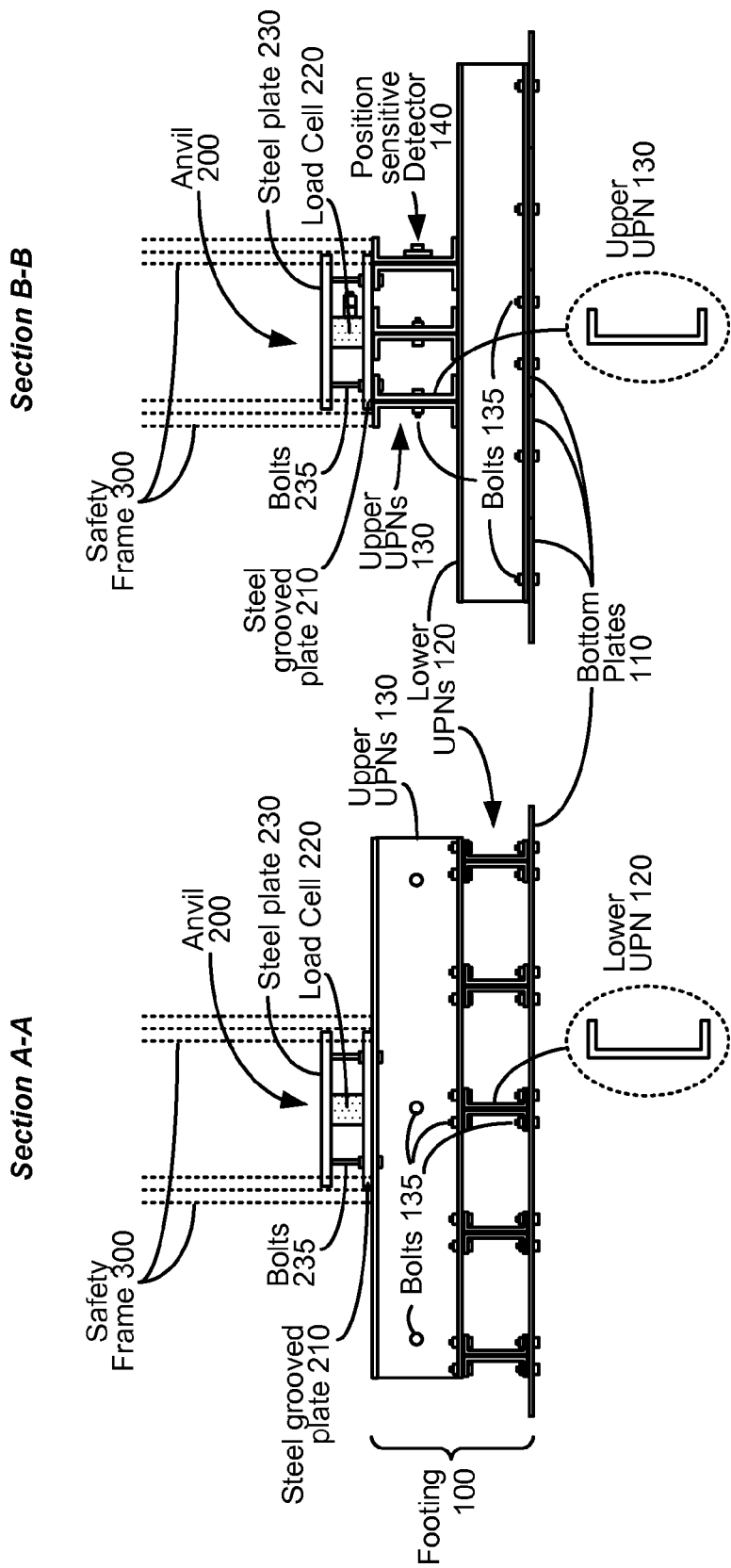
FIG. 3 presents perpendicular sectional views of the steel footing 100 through the center of the footing. These sectional views clarify the fastening points of the steel members (110, 120, 130) as well as the location of the electronic instrumentation (the position sensitive detector 140, and load cell 220).

At the discretion of the project engineer, soil conditions at the intended test location 50 are determined by collection of soils samples by soil boring, test pit, or bucket sample. Further material testing is additionally performed to classify the subsurface material and determine strength/compressibility properties.

The steel footing 100 beams 120 and 130, drop weight plates 480, and electronic accessories are delivered to the site location. When unassembled, the maximum weight of any single steel member is 150 kg. This allows a crew of four laborers to move pieces around the site location by hand. A boom truck is a convenient vehicle to use as it allows mobilization of steel members to a project site by road and facilitates unloading of the vehicle. The steel members are placed around the intended test location as designated by the project surveyor or engineer. The steel footing 100 and drop weight 400 are assembled by hand. Footing 100 comprises upper channel (UPN) beams 130, lower UPN beams 120, and bottom plates 110 bolted together via bolts 135 as shown in the Figures. An optional 7 T (ton) crane 420 will facilitate the work of the labor crew but is not expressly required. The footing 100 and anvil 200 are fastened together, with anvil 200 comprising a lower steel grooved plate 210 and an upper steel plate 230 held together and fastened to the upper UPN beams 130 of the footing 100 by bolts 235 as shown in the Figures. Steel angle and channel sections are comprised of Grade 235 steel or any mild steel with a minimum yield strength of 235 MPa. Steel plate sections are comprised of Grade 509 steel or any carbon steel with a minimum yield strength of 509 MPa. The load cell 220 is placed within the anvil 200 between steel plate 230 and steel grooved plate 210, and the anvil 200 is fastened to the footing 100 by the bolts 235. A slab of plywood or neoprene 1" thick (not shown) is optionally placed on top of the anvil 200 within the dimensions of the safety frame 300 to assist distribution of the load from eccentric impacts.

The load cell 220 has a minimum capacity of 80 T. The use of a load cell 220 with a capacity larger than the anticipated load compromises the resolution and accuracy of the load measurement but reduces the possibility of deformation of the load cell housing during multiple tests under repeated impacts. The resolution of the load cell 220 is less than 0.1% of the full scale load. The accuracy of the load cell 220 is not larger than ±1% of the full scale load. The analog output of the load cell 220 ranges between 1 to 5 mV/V.

The position sensitive detector (PSD) 140 is fastened to the footing 100 using a 6 mm diameter stainless steel bolt. The fastening point is the flange of a beam 120 or 130 spanning the steel footing 100. A steel nut is welded to the flange to secure the bolt fastened to the PSD 140. The analog output of the PSD 140 ranges between 1 to 10 V. The typical resolution of the PSD 140 ranges between 500 to 800 nm. The red laser 150 is a Class II laser generating a laser pulse at a wavelength of 635 nm and at a power less than 1 mW. Shortpass and longpass optical filters with dielectric hard coatings are fastened using adhesives to the PSD 140's housing to block light illuminating the PSD 140 at wave lengths less than 635 nm and greater than 670 nm. The red laser 150 is mounted on a short tripod 151 at a minimum distance 5 m away from the footing 100 and the laser beam 152 is aligned to shine on the PSD 140.

The acquisition system (not shown) is connected to the PSD 140 and the load cell 220. The acquisition system for the PSD 140 consists of an analog to digital converter. The acquisition system for the load cell 220 consists of an analog to digital converter using a full bridge strain module. The full bridge strain module is capable of 24 bit resolution and delivery of a suitable excitation voltage on the order of 1V to 10V to the load cell 220. The acquisition system uses screw terminals to facilitate connection of instrumentation data cables to the acquisition terminals. The converted digital signal is acquired using a computer program on a laptop computer (not shown). Prior to commencing the test, the digital signal is checked to ensure that the instruments are responsive, and that measurements will remain within the instrumentation range. Review of the signal ensures the initial load cell 220 reading is a zero load signal. Sampling frequency of both analog signals is set to a minimum 5 kHz.

The acquisition system acquires converted digital signals simultaneously by using a single acquisition computer program on the acquisition laptop.

Once the steel footing 100 and drop weight 400 are assembled, a mobile crane 420 of a minimum 7 T capacity is mobilized to conduct the test. The crane 420 places the drop weight 400 on the anvil 200 and within the safety frame 300. A lineman 95 attaches a release hook 410 to the drop weight 400 and the crane driver lifts the drop weight. The drop weight 400 is placed within the confines of the safety frame 300 and the release hook 410 is disengaged. The safety frame 300 ensures the drop weight 400 lands on the anvil 200 and does not rebound onto the steel footing 100. The lineman 95 attaches the release hook 410 to the crane 420 and drop weight 400. When the drop weight 400 is secured, the crane driver lifts the weight 400 using the quick release hook 410. The quick release hook 410 will allow the drop weight 400 to drop in free fall onto the anvil 200. The test arrangement prior to release of the drop weight 400 is illustrated in FIG. 1.

A seating drop at about 5 cm above the anvil 200 is performed. When the drop weight 400 is at the required height, the lineman 95 pulls the release line 96 and the drop weight 400 is released. The drop weight 400 strikes the anvil 200 and remains within the safety frame 300.

An additional three drop heights are designated by the project engineer. In the absence of such an instruction, the nominal drop heights of the drop weight 400 above the anvil 200 are 0.5 m, 1.0 m, and 1.5 m. Following the completion of the third drop height, the test is concluded. The supervising engineer performs additional drops at varying heights and at their discretion. Following conclusion of the test, the equipment is unfastened and loaded into a vehicle for demobilization from the location.

The embodiments of the invention which are claimed are described in the following section.

I claim:

1. A test system for testing a soil foundation, comprising:
    a footing comprising a plurality of lower channel beams oriented in a first direction, and a plurality of upper channel beams oriented in a second direction perpendicular to the first direction, wherein a bottom planar surface of the footing is positionable on a surface of the soil foundation, the footing further comprising a position sensitive detector;
    an anvil connected to a top planar surface of the footing, the anvil further comprising a load sensor, wherein the anvil comprises a top plate and a bottom plate, and wherein the load sensor is positioned between the top plate and the bottom plate; and
    a drop weight configured to be dropped on the anvil from a drop height; and
    an acquisition system configured to acquire signals from the position sensitive detector and the load sensor when the drop weight is dropped on the anvil.

2. The test system of claim 1, wherein the acquisition system is configured to determine a vertical displacement of the soil foundation as a function of time.

3. The test system of claim 1, wherein the position sensitive detector is used to indicate a vertical displacement of the soil foundation when the drop weight is dropped on the anvil.

4. The test system of claim 1, further comprising a frame, wherein the drop weight is configured to be positioned within the frame when it is dropped onto the anvil.

5. The test system of claim 1, further comprises a release hook and release line, wherein the release hook is configured to drop the drop weight on the anvil when the release line is engaged.

6. The test system of claim 5, wherein the release hook is configured to be suspended by mobile crane.

7. The test system of claim 1, wherein the position sensitive detector comprises a photo detector.

8. The test system of claim 7, further comprising a laser source for illuminating the position sensitive detector, wherein the position sensitive detector is configured to determine a vertical displacement of the soil foundation when the drop weight is dropped on the anvil.

9. The test system of claim 1, wherein the load sensor comprises an electrical resistance strain gauge load cell.

10. A method for testing a soil foundation at a site, comprising:
    constructing a temporary footing comprising a plurality of lower channel beams oriented in a first direction, and a plurality of upper channel beams oriented in a second direction perpendicular to the first direction;
    positioning a bottom planar surface of the footing on a surface of the soil foundation at the site;
    connecting an anvil to a top planar surface of the footing, wherein the anvil comprises a top plate and a bottom plate, and wherein a load sensor is positioned between the top plate and the bottom plate;
    dropping a drop weight onto the anvil from at least one drop height to cause the footing to vertically displace into the soil foundation;
    acquiring a signal from a position sensitive detector affixed to the footing and from the load sensor to determine the amount of vertical displacement of the footing on the soil foundation; and
    dismantling the footing and removing the footing from the site.

11. The method of claim 10, further comprising determining vertical displacement of the footing on the soil foundation as a function of time.

12. The method of claim 10, wherein the position sensitive detector comprises a photo detector.

13. The method of claim 12, further comprising illuminating the position sensitive detector with a laser beam from a laser on the soil surface.

14. The method of claim 10, further comprising constructing a frame, wherein the drop weight is positioned within the frame when it is dropped.

15. The method of claim 10, wherein the drop weight is dropped from an increasing plurality of drop heights.

16. The method of claim 10, wherein the drop weight is dropped by engaging a release line connected to a release hook connected to the drop weight.

* * * * *